United States Patent [19]

Sumioka et al.

[11] Patent Number: 5,561,028
[45] Date of Patent: Oct. 1, 1996

[54] SILVER HALIDE PHOTOGRAPHIC PHOTOSENSITIVE MATERIAL

[75] Inventors: Ko-ichi Sumioka; Akira Tanaka, both of Tokyo, Japan

[73] Assignee: Mitsubishi Paper Mills Limited, Tokyo, Japan

[21] Appl. No.: 460,796

[22] Filed: Jun. 2, 1995

[30] Foreign Application Priority Data

Jun. 24, 1994 [JP] Japan .................................. 6-143263

[51] Int. Cl.$^6$ .............................................. G03C 1/06
[52] U.S. Cl. ........................ 430/264; 430/434; 430/448; 430/598
[58] Field of Search .................... 430/264, 598, 430/434, 448

[56] References Cited

U.S. PATENT DOCUMENTS

| | | | |
|---|---|---|---|
| 2,419,975 | 5/1947 | Trivelli et al. | 430/448 |
| 2,527,583 | 10/1950 | Silberstein et al. | 430/507 |
| 2,533,472 | 12/1950 | Keyes et al. | 430/522 |
| 2,956,879 | 10/1960 | Van Campen | 430/507 |
| 3,148,187 | 9/1964 | Heseltine | 430/522 |
| 3,177,078 | 8/1965 | Bockly et al. | 430/522 |
| 3,247,127 | 4/1966 | Bailey | 430/507 |
| 3,314,794 | 4/1967 | Sawdey | 430/507 |
| 3,352,681 | 11/1967 | Ohi et al. | 430/512 |
| 3,384,487 | 5/1968 | Heseltine et al. | 99/334 |
| 3,423,207 | 11/1969 | Heseltine et al. | 430/522 |
| 3,486,897 | 12/1969 | Oliver | 430/522 |
| 3,499,762 | 3/1970 | Cressman et al. | 430/517 |
| 3,533,794 | 10/1970 | Ohi et al. | 430/512 |
| 3,540,887 | 11/1970 | Depoorter et al. | 430/580 |
| 3,575,704 | 4/1971 | Salesin | 430/949 |
| 3,652,283 | 3/1972 | Mackey | 430/522 |
| 3,653,905 | 4/1972 | Depoorter et al. | 430/522 |
| 3,700,455 | 10/1972 | Ishikawa et al. | 430/551 |
| 3,705,805 | 12/1972 | Nittel et al. | 430/512 |
| 3,707,375 | 12/1972 | Ohi et al. | 430/517 |
| 3,718,472 | 2/1973 | Oliver et al. | 430/517 |
| 3,976,661 | 8/1976 | Brooker et al. | 548/400 |
| 4,045,229 | 8/1977 | Weber, II et al. | 202/93 |
| 4,166,742 | 9/1979 | Mifune et al. | 430/568 |
| 4,168,977 | 9/1979 | Takada et al. | 430/446 |
| 4,211,857 | 7/1980 | Sugio et al. | 528/215 |
| 4,224,401 | 9/1980 | Takeda et al. | 430/437 |
| 4,269,929 | 5/1981 | Nothnagle | 430/949 |
| 4,272,606 | 6/1981 | Mifune et al. | 430/264 |
| 4,311,781 | 1/1982 | Mifune et al. | 430/264 |
| 4,385,108 | 5/1983 | Takagi et al. | 430/264 |
| 4,429,036 | 1/1984 | Hirano et al. | 432/264 |
| 4,459,347 | 7/1984 | Parton et al. | 430/217 |
| 4,789,618 | 12/1988 | Inoue et al. | 430/264 |
| 4,800,150 | 1/1989 | Katoh | 430/264 |
| 4,975,354 | 12/1990 | Machonkin et al. | 430/264 |

*Primary Examiner*—Lee C. Wright
*Attorney, Agent, or Firm*—Cushman Darby & Cushman

[57] ABSTRACT

Provided is a silver halide photographic photosensitive material excellent in rapid processability and having high processing stability which contains at least one compound represented by the following formula (I) and (II):

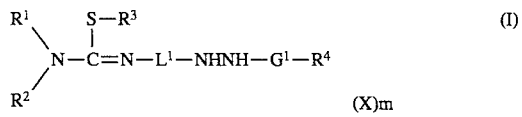

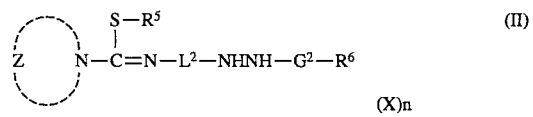

wherein $L^1$ and $L^2$ each represent a divalent linkage group, $G^1$ and $G^2$ each represent a carbonyl group, a sulfonyl group, a sulfinyl group, an oxalyl group or a phosphoryl group, $R^1$ and $R^2$ each represent a hydrogen atom, an alkyl group, an aralkyl group, an alkenyl group or an aryl group, $R^3$ and $R^5$ each represent an alkyl group, an aralkyl group or an alkenyl group, $R^4$ and $R^6$ each represent a hydrogen atom, an alkyl group, an alkoxy group, an aryloxy group, an aryl group or an amino group, Z represents a group of atoms necessary to form a nitrogen-containing 5- to 18-membered ring, X represents a counter ion, and m and n each represent 0 or 1, and the isothioureido group may be a salt of a protonic acid.

5 Claims, No Drawings

SILVER HALIDE PHOTOGRAPHIC PHOTOSENSITIVE MATERIAL

BACKGROUND OF THE INVENTION

The present invention relates to a silver halide photographic photosensitive material and a method for forming superhigh contrast negative images using the photosensitive material, and in particular to a silver halide photographic photosensitive material used for photomechanical process.

In the field of graphic arts, image forming systems which can provide photographic characteristics of superhigh contrast (especially, at least 10 in gamma value) are necessary to make it possible to perform good reproduction of line images or continuous tone images comprising dot images. For obtaining photographic characteristics of high contrast using stable developers, use of hydrazine derivatives has been known as described in U.S. Pat. Nos. 4,166,742, 4,168,977, 4,211,857, 4,224,401, 4,311,781 and 4,272,606. According to these methods, photographic characteristics of superhigh contrast and high sensitivity can be obtained and furthermore, developers can contain sulfites in a high concentration. Therefore, stability of developers against oxidation with air is markedly higher than lith developers. However, it is known that conventional hydrazine compounds have some defects. Thus, it has been attempted to make the conventional hydrazine compounds have an undiffusible structure for the purpose of diminishing adverse effects on other photographic photosensitive materials owing to their flowing out into developers. Such undiffusible hydrazine compounds are needed to be used in a large amount for sensitization and enhancement of contrast and as a result, physical strength of the resulting photosensitive layer is deteriorated or the hydrazine compounds precipitate in the coating solutions. Moreover, when the photosensitive materials are processed with exhausted developers which have been used for processing of a lot of photosensitive materials, sufficiently high contrast cannot be obtained. Furthermore, since the superhigh contrast systems using hydrazine compounds require developers of relatively high pH, for example, 11.5 or 11.8, there are problems such as high dangerousness in handling and large BOD and COD in disposal of waste solutions. In addition, since the pH buffers for keeping constant the pH of developers must be used in a large amount, solid concentration of developers increases and the developers become viscous, and the scattered developers are difficult to wipe off. Thus, development of hydrazine compounds which can provide high contrast using developers of lower pH has been desired. Furthermore, in general, reversal photosensitive materials handled under roomlight occupy a large field as one of photomechanical photosensitive materials, and in this field, demanded is a high extractability of letters enough to be able to reproduce even the fine Ming letters. For this purpose, development of nucleating agents higher in activity has been demanded. Especially, for roomlight photosensitive materials of low sensitivity capable of being handled even under roomlight, development of nucleating agents which hardly cause increase of contrast and have higher activity has been desired.

SUMMARY OF THE INVENTION

The first object of the present invention is to provide a silver halide photographic photosensitive material for photomechanical process which is excellent in rapid processability and has a high processing stability. The second object of the present invention is to provide a silver halide photographic photosensitive material for photomechanical process which can be developed at a low pH.

The above objects have been attained by silver halide photographic photosensitive materials which contain at least one compound represented by the following formulas (I) and (II):

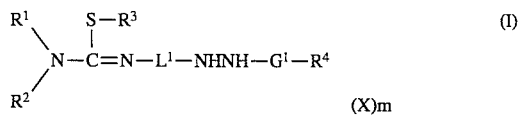

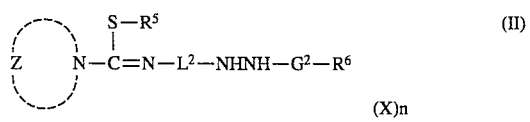

wherein $L^1$ and $L^2$ each represent a divalent linkage group, preferably an arylene group, especially preferably a phenylene group. It may have a known substituent on carbon atoms. Examples of the substituent are alkyl group, alkenyl group, alkynyl group, alkoxy group, hydroxy group, halogen atom, amide group, sulfonamide group, etc. $G^1$ and $G^2$ each represent a carbonyl group, a sulfonyl group, a sulfinyl group, an oxalyl group or a phosphoryl group, and preferred are carbonyl group and oxalyl group. $R^3$ and $R^5$ each represent a hydrogen atom, an alkyl group, an aralkyl group, an alkenyl group or an aryl group and $R^3$ and $R^5$ each represent an alkyl group, an aralkyl group or an alkenyl group. Of these alkyl group, aralkyl group and alkenyl group, preferred are those which have 1–30 carbon atoms and especially preferred are those which have 1–20 carbon atoms. The aryl group is preferably monocyclic or dicyclic. These $R^1$–$R^3$ and $R^5$ may have known substituents. Typical examples of the substituents are alkyl group, alkenyl group, alkynyl group, alkoxy group, aryl group, aryloxy group, sulfamoyl group, ureido group, urethane group, carbamoyl group, alkylthio group, arylthio group, alkylsulfonyl group, arylsulfonyl group, hydroxy group, halogen atom, cyano group, aryloxycarbonyl group, acyl group, alkoxycarbonyl group, acyloxy group, amide group, sulfonamide group and carboxy group.

$R^4$ and $R^6$ each represents a hydrogen atom, an alkyl group, an alkoxy group, an aryloxy group, an aryl group or an amino group. When $G^1$ and $G^2$ are carbonyl groups, $R^4$ and $R^6$ are preferably hydrogen atom, alkyl groups (e.g., methyl group, trifluoromethyl group, 3-hydroxypropyl group, 3-methanesulfonamidopropyl group, phenylsulfonylmethyl group, 2-hydroxybenzyl group, trimethylammoniomethyl group, triethylammoniomethyl group, (1-pyridinio)methyl group, (4-methyl-1-pyridinio)methyl group, (3-methyl-1-imidazolio)methyl group, etc.) and aryl groups (e.g., phenyl group, 3,5-dichlorophenyl group, o-methanesulfonamidophenyl group, 4-methanesulfonylphenyl group, 2-hydroxymethylphenyl group, etc.). Especially preferred are hydrogen atom and substituted alkyl groups having quaternary nitrogen atom in the structure. When $G^1$ and $G^2$ are sulfonyl group, sulfinyl group and oxalyl group, $R^4$ and $R^6$ are preferably alkoxy groups (e.g., methoxy group, ethoxy group, etc.), aryloxy groups (e.g., phenoxy group, 4-chlorophenoxy group, etc.) and amino groups. Especially preferred are substituted amino groups having at least one hydroxy group or amino group in the structure (e.g., 2-hydroxyethylamino group, 3-hydroxypropylamino group, 3-hydroxy-2,2-dimethylpropylamino group, 2,3-dihydroxypropylamino group, 2-hydroxymethylanilino group, 2-dimethylaminoethylamino group, 2-diethylaminoethylamino group, 2-dipropylaminoethylamino group, 2-dibutylaminoethylamino group, 3-dimethylaminopropylamino group, 3-diethylaminopropylamino group, 3-dipropylaminopropylamino group, 3-dibutylaminopropylamino group, etc.) and substituted amino groups having quaternary nitrogen atom (e.g., 2-trimethylammonioethylamino group, 2-triethylammonioethylamino group, 2-tripropylammonioethylamino group, 2-tributylammonioethylamino group, 3-trimethylammoniopropylamino group, 3-triethylammoniopropylamino group, 3-tripropylammoniopropylamino group, 3-tributylammoniopropylamino group, (1-methyl-3-pyridinio)amino group, (1-ethyl-3-pyridinio)amino group, (1-propyl-3-pyridinio)amino group, (1-butyl-3-pyridinio)amino group, etc.). When $G^1$ and $G^2$ are phosphoryl group, $R^4$ and $R^6$ are preferably methoxy group, ethoxy group, butoxy group, phenoxy group, phenyl group, etc.

Furthermore, $R^1$–$R^3$ and $R^5$ may be those which contain ballasts which are customarily used in inert photographic additives such as couplers. Ballasts are groups having 8 or more carbon atoms and relatively inert to photographic properties and can be selected, for example, from alkyl group, phenyl group, alkylphenyl group, phenoxy group, alkylphenoxy group, etc. Moreover, $R^1$–$R^3$ and $R^5$ may contain groups which strengthen adsorption to the surface of silver halide grains. Such adsorption groups include, for example, heterocyclic thioamide groups, mercapto heterocyclic groups and triazole groups which are described in U.S. Pat. Nos. 4,385,108 and 4,459,347, and Japanese Patent Kokai Nos. 59-195233, 59-200231, 59-201045, 59-201046, 59-201047, 59-201049, 61-170733, 61-270744, 62-948, 63-234244, 63-234245 and 63-234246.

Z represents a group of atoms necessary to form a nitrogen-containing 5- to 18-membered ring (e.g., pyrrolidine, piperidine, hexamethyleneimine, piperazine, morpholine, thiomorpholine, monoaza crown ether-12, 15, 18, etc.). The preferred rings are those of 4–30, preferably 4–20 carbon atoms which contain on the ring the substituents such as those exemplified for $R^1$–$R^3$ and $R^5$. X represents a counter ion (e.g., halogen ion such as Cl$^-$, Br$^-$ or I$^-$, 4-toluenesulfonate, etc.), and m and n each represent 0 or 1. The isothioureido group in the formulas may be in the form of a salt with protonic acids (e.g., hydrochloric acid, hydrobromic acid, hydriodic acid, perchloric acid, methanesulfonic acid, 4-toluenesulfonic acid, sulfuric acid, etc.).

When $R^1$ is hydrogen atom and $R^2$ is an aryl group, there is the possibility of existing a tautomerism between the following formulas.

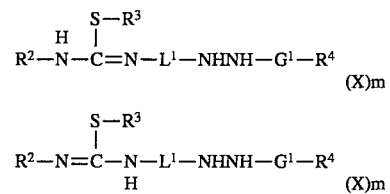

Examples of the compounds used in the present invention are enumerated below. The present invention is not limited thereto.

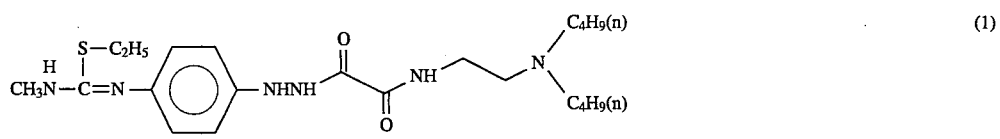

(1)

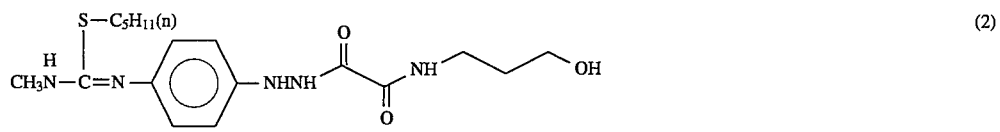

(2)

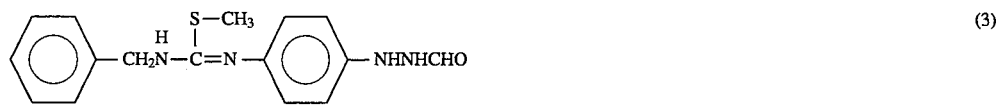

(3)

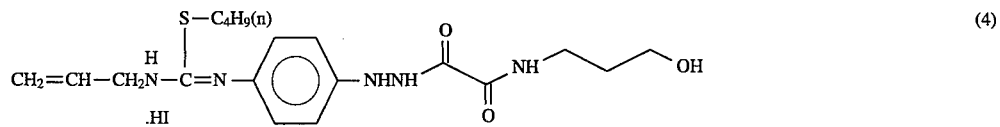

(4)

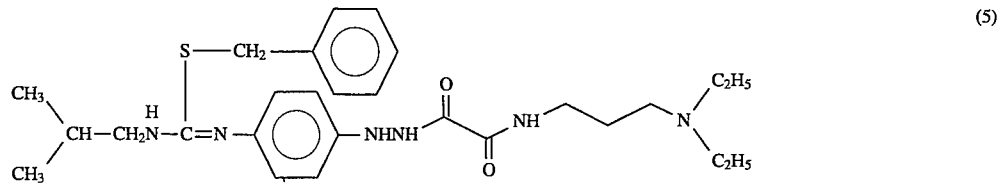

(5)

-continued
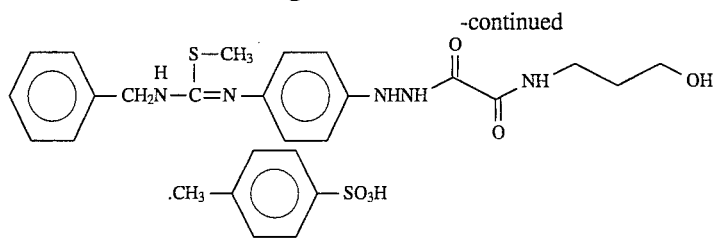(6)
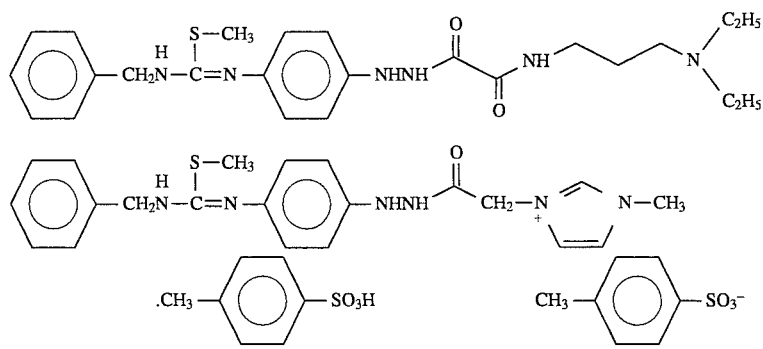(7)
(8)
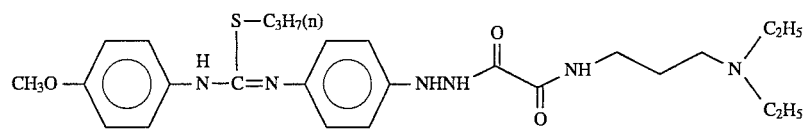
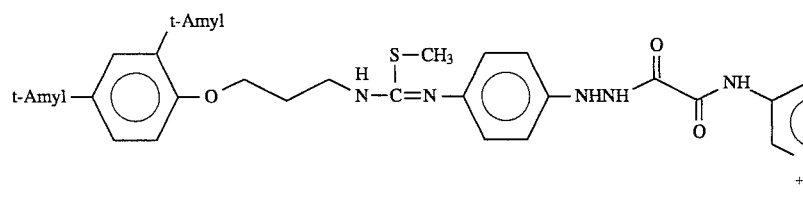(9)
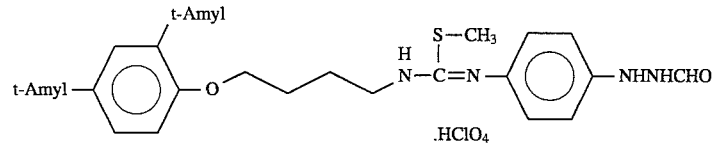(10)
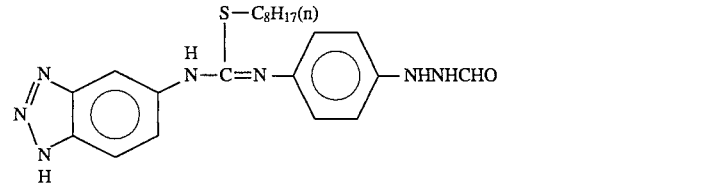(11)
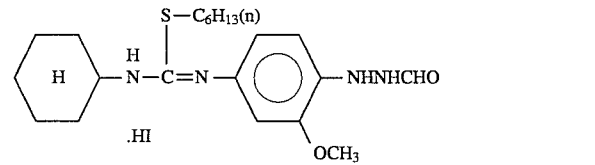(12)
(13)
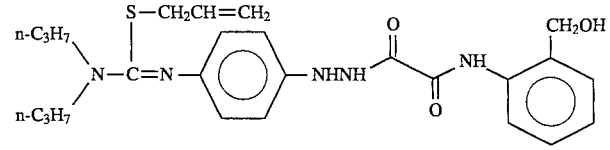(14)

-continued

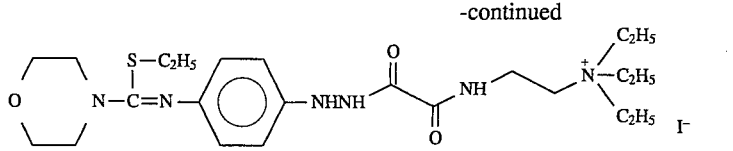 (15)

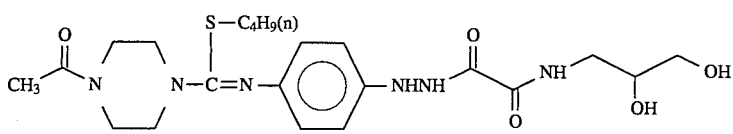 (16)

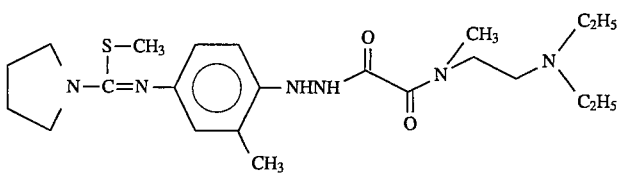 (17)

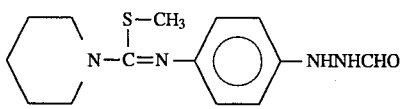 (18)

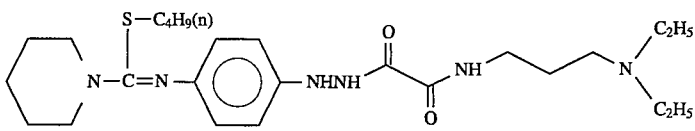 (19)

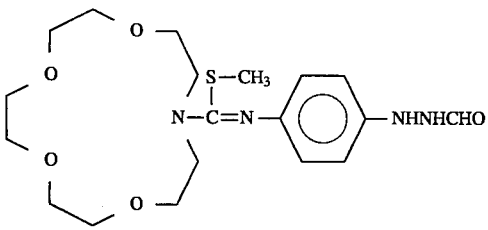 (20)

The hydrazine derivatives represented by the formulas (I) and (II) used in the present invention can be easily obtained, for example, by neutralizing with a base an isothiouronium salt synthesized by the reaction of a thioureidophenylhydrazine with an alkylating, aralkylating or alkenylating agent (e.g., alkyl halide, aralkyl halide and alkenyl halide, alkyl sulfonate, aralkyl sulfonate and alkenyl sulfonate esters, etc.). The thioureidophenylhydrazines are synthesized, for example, by (1) reaction of aminophenylhydrazines with isothiocyanates, (2) reaction of amines with phenoxythioamidophenylhydrazines synthesized from aminophenylhydrazines and o-phenyl chlorothioformate. A typical synthesis example is shown below.

Synthesis Example

Synthesis of compound (2):

8.9 g of 1-ethoxalyl-2-(4-aminophenyl)hydrazine and 3.0 g of methyl isothiocyanate were added to 75 ml of ethanol, followed by refluxing for 3.5 hours under heating. The refluxed product was left to stand for cooling and the precipitated crystal was collected by filtration, washed with ethanol and then dried to obtain 8.6 g of 1-ethoxalyl-2-[4-(3-methylthioureido)phenyl]hydrazine (intermediate A) having a melting point of 168°–169° C.

4.4 g of the intermediate A and 1.5 g of 3-amino-1-propanol were added to 30 ml of acetonitrile, followed by refluxing for 1 hour under heating. The precipitated crystal was collected by filtration, washed with acetonitrile and ether successively and then dried to obtain 4.6 g of 1-[3-(3-hydroxypropyl)oxamoyl]-2-[4-(3-methylthioureido)phenyl]hydrazine (intermediate B) having a melting point of 217°–218° C.

1.30 g of the intermediate B, 0.79 g of 1-iodopentane and 7 ml of sulfolane were mixed and the mixture was stirred at 100° C. for 4 hours with heating. Then, thereto were added 30 ml of methylene chloride and 30 ml of 0.5N aqueous sodium hydrogencarbonate solution, followed by stirring at room temperature for 10 minutes. The methylene chloride layer was separated, washed with water (twice with 50 ml of water), and dried (over anhydrous sodium sulfate), and the solvent was removed. The residue was purified by silica gel column chromatography (chloroform/methanol=8/1) to obtain 0.80 g of the compound (2) having a melting point of 132°–134° C.

The hydrazine derivatives used in the present invention can be used as solutions in suitable water-miscible organic solvents such as alcohols (e.g., methanol, ethanol and propanol), ketones (e.g., acetone and methyl ethyl ketone), N,N-dimethylformamide, dimethyl sulfoxide and methyl cellosolve. Furthermore, the hydrazine derivatives can be dissolved in oils such as dimethyl phthalate, tricresyl phosphate, glyceryl triacetate and diethyl terephthalate or co-solvents such as ethyl acetate and cyclohexanone by the well-known emulsification dispersing method to prepare mechanically emulsification dispersion. Moreover, a method known as solid dispersing method by colloid mills, ball mills and ultrasonic waves can also be applied.

The silver halides used for photosensitive silver halide emulsion layers of the photosensitive materials of the present invention have no special limitation, but are preferably surface latent image type silver halide emulsions. Examples of the silver halides usable are silver chloride, silver chlorobromide, silver chloroiodobromide, silver iodobromide and silver bromide. When silver iodobromide or silver chloroiodobromide is used, content of silver iodide is preferably in the range of 5 mol % or less. Form, crystal habit and size distribution of silver halide grains are not limitative, but preferred are those which have a grain size of 0.7 micron or smaller. The sensitivity of the silver halide emulsion can be increased with gold compounds such as chloroaurates and gold trichloride, salts of noble metals such as rhodium and iridium, sulfur compounds capable of forming silver sulfide upon reacting with silver salts, or reducing materials such as stannous salts and amines without coarsening the grains. Furthermore, salts of noble metals such as rhodium and iridium or iron compounds such as pottasium ferricyanate can also be allowed to be present at the time of physical ripening of silver halide grains or at the time of nucleation. Especially, addition of rhodium salts or complexes thereof can further accelerate the effect of the present invention of attaining superhigh contrast photographic characteristics in a short developing time and they are preferred.

The surface latent image type silver halide emulsion in the present invention means an emulsion comprising silver halide grains having a surface sensitivity higher than inner sensitivity and this emulsion preferably has a difference between the surface sensitivity and the inner sensitivity as specified in U.S. Pat. No. 4,224,401. The silver halide emulsion is preferably a monodispersed emulsion and especially preferably an emulsion having the monodispersibility specified in the above U.S. Pat. No. 4,224,401. The silver halide emulsion used in the present invention preferably contains a water-soluble rhodium salt (e.g., rhodium dichloride, rhodium trichloride, potassium hexachlororhodate (III), ammonium hexachlororhodate (III), etc.). These rhodium salts are preferably added before completion of the first ripening in preparation of emulsions. Amount of the rhodium salts is preferably $1 \times 10^{-7}$ to $1 \times 10^{-4}$ mol for 1 mol of silver halide. Average grain size of the silver halide used in the present invention is preferably 0.5 μm or less, especially preferably in the range of 0.1–0.4 μm. The silver halide grains may be in regular form, for example, cube or octahedron, or may be mixed crystal, but are preferably of so-called monodispersed emulsion having a relatively narrow grain size distribution. The monodispersed emulsion here means an emulsion in which at least 90%, preferably at least 95% of total grains have a size within ±40% of the average size. For reacting a soluble silver salt with a soluble halogen salt to prepare the silver halide emulsion in the present invention, there may be employed any means such as single jet method, double jet method and reverse mixing method which forms the grains in the presence of excess silver ions. However, for the object of the present invention, especially preferred is the double jet method by which the soluble silver salt and the soluble halogen salt are simultaneously added in the presence of an acidic solution to form the grains. The thus prepared silver halide emulsion may be or may not be chemically sensitized. It is rather preferred that the silver halide emulsion is not chemically sensitized from the viewpoint of improving handleability of the photosensitive materials under the environment of safelight which can be called substantially roomlight. When chemical sensitization is conducted, it is carried out by usual sulfur sensitization, reduction sensitization, noble metal sensitization (e.g., gold sensitization).

The compound represented by the formula (I) or (II) is preferably contained in the surface latent image type silver halide emulsion layer in the photosensitive material of the present invention, but it may be contained in a hydrophilic colloid layer contiguous to the surface latent image type silver halide emulsion layer. Such hydrophilic colloid layer may be any layers having any function, for example, undercoat layer, intermediate layer, filter layer, protective layer and antihalation layer as far as diffusion of the compound represented by the formula (I) or (II) into the silver halide grains is not hindered. Content of the compound varies depending on properties of the silver halide emulsion used, chemical structure of the compound used and developing conditions, and suitable content can be changed in a wide range, but a range of about $1 \times 10^{-6}$ to $1 \times 10^{-2}$ mol for 1 mol of silver in the surface latent image type silver halide emulsion is practically preferred.

The photographic emulsion used in the present invention may be spectrally sensitized with methine dyes and others. These dyes include cyanine dyes, merocyanine dyes, composite cyanine dyes, composite merocyanine dyes, holopolar cyanine dyes, hemicyanine dyes, styryl dyes, and hemioxonol dyes. Especially preferred are those which belong to cyanine dyes, merocyanine dyes and composite merocyanine dyes. These sensitizing dyes may be used each alone or in combination of two or more. The sensitizing dyes are often used in combination for the purpose of super sensitization. The emulsion may contain together with the sensitizing dyes a dye which per se has no spectral sensitizing action or a material which absorbs substantially no visible light and shows supersensitization. Useful sensitizing dyes, combination of sensitizing dyes for supersensitization and materials which show supersensitization are described in "Research Disclosure", vol. 1.176, 17643 (December 1978), page 23, IV-J.

As binders or protective colloids used in the emulsion layer, intermediate layer and others of the photosensitive materials of the present invention, gelatin is useful, but other hydrophilic colloids may also be used. Examples of these hydrophilic colloids are gelatin derivatives, graft polymers of gelatin with other polymers, proteins such as albumin and casein, cellulose derivatives such as hydroxyethyl cellulose, carboxymethyl cellulose and cellulose sulfate esters, sugar derivatives such as sodium alginate and starch derivatives, and various synthetic hydrophilic polymer materials such as homopolymers, e.g., polyvinyl alcohol, partial acetals of polyvinyl alcohol, poly-N-vinylpyrrolidone, polyacrylic acid, polymethacrylic acid, polyacrylamide, and polyvinylimidazole, and copolymers thereof. As the gelatins, there may be used lime-treated gelatins and furthermore, acid-treated gelatins and enzyme-treated gelatins described in Bull. Soc. Sci. Phot. Japan, No.16, p 30 (1966). Moreover, there may be used hydrolyzates of gelatins and enzyme-decomposition products of gelatins.

The photographic emulsions used in the present invention may contain various compounds for the purpose of inhibiting occurrence of fog during preparation and storage of the photosensitive materials or during photographic processing or for the purpose of stabilizing photographic performances. Examples of these compounds are azoles such as nitroimidazoles, nitrobenzimidazoles, chlorobenzimidazoles, mercaptothiazoles, mercaptobenzothiazoles, mercaptothiadiazoles, aminotriazoles, benzotriazoles and mercaptotetrazoles, mercaptopyrimidines, mercaptotriazines, thioketo compounds, azaindenes and benzothiazolium salts. These compounds have been known as antifoggants or stabilizers. Of these compounds, especially preferred are benzotriazoles such as 5-methylbenzotriazole and nitroindazoles such as 5-nitroindazole. These compounds may be contained in a processing solution.

The photographic photosensitive materials of the present invention may contain inorganic or organic hardeners in photographic emulsion layers and other hydrophilic colloid layers. Examples of the hardeners are chromium salts such as chrome alum, aldehydes such as formaldehyde and glyoxal, N-methylol compounds, dioxane derivatives such as 2,3-dihydroxydioxane, active vinyl compounds, active halogen compounds such as 2,4-dichloro-6-hydroxy-S-triazine. These are used each alone or in combination of two or more.

The photographic emulsion layers or other hydrophilic colloid layers may contain surface active agents for various purposes as coating aids and antistatic agents and for improvement of slipperiness, emulsification dispersing, prevention of adhesion and improvement of photographic characteristics (such as acceleration of development, enhancement of contrast and sensitization). Examples of the surface active agents are nonionic surface active agents such as saponins (steroid type), alkylene oxide derivatives (such as polyethylene glycol, polyethylene glycol/polypropylene glycol condensates, polyethylene glycol alkyl ethers or polyethylene glycol alkylaryl ethers, polyethylene glycol esters, polyethylene glycol sorbitan esters, polyalkylene glycol alkylamines or amides and polyethylene oxide adducts of silicon), glycidol derivatives (such as polyglyceride alkenylsuccinate and alkylphenol polyglycerides), fatty acid esters of polyhydric alcohols and alkyl esters of sugars, anionic surface active agents containing acidic groups such as carboxyl group, sulfo group, phospho group, sulfate ester group and phosphate ester group, for example, alkylcarboxylates, alkylsulfates, alkylbenzenesulfonates, alkylphosphates, sulfosuccinates, sulfoalkylpolyoxyethylene alkylphenyl ethers and polyoxyethylenealkylphosphates and amphoteric surface active agents such as amino acids, aminoalkylsulfonic acids and aminoalkylsulfates or aminoalkylphosphate esters, and cationic surface active agents such as aliphatic or aromatic quaternary ammonium salts and heterocyclic quaternary ammonium salts such as pyridinium and imidazolium.

The photographic photosensitive materials of the present invention can contain water-insoluble or slightly water-soluble synthetic polymer decomposition products in the photographic emulsion layers or other hydrophilic colloid layers for the purpose of improvement of dimensional stability. Examples of the polymers are those which contain as monomer components one or more of alkyl (meth)acrylates, alkoxyalkyl (meth)acrylates, glycidyl (meth)acrylates, (meth)acrylamides, vinyl acetate, acrylonitrile, olefins and styrene or combination of these monomers with acrylic acid, methacrylic acid, $\alpha,\beta$-unsaturated dicarboxylic acid, hydroxyalkyl (meth)acrylates or styrenesulfonic acid.

The photosensitive materials of the present invention may contain organic desensitizers. Preferred are those which contain at least one water-soluble group or alkali dissociative group. These organic desensitizers are described in Japanese Patent Kokai No.63-64039. When organic desensitizers are used, it is suitable to use them in an amount of $1.0\times10^{-8}$ to $1.0\times10^{-4}$ mol/m$^2$, preferably $1.0\times10^{-7}$ to $1.0\times10^{-5}$ mol/m$^2$.

The photosensitive materials of the present invention may contain development accelerators. As suitable development accelerators or nucleating infectious development accelerators, various compounds containing N or S atom as well as the compounds disclosed in Japanese Patent Kokai Nos. 53-77616, 53-137133, 54-37732, 60-140340, 62-222241, 63-124045 and 2-294637, and U.S. Pat. No. 4,975,354 are effective. The optimum amount of these accelerators varies depending on the kinds of them, but it is desirable to use them in an amount of $1.0\times10^{-3}$ to 0.5 g/m$^2$, preferably $5.0\times10^{-3}$ to 0.1 g/m$^2$. These accelerators are dissolved in suitable solvents, e.g., water, alcohols such as methanol and ethanol, acetone, N,N-dimethylformamide and methyl cellosolve and added to coating solutions. These additives may be used in combination of two or more. The emulsion layers or other hydrophilic colloid layers may contain water-soluble dyes as filter dyes or for the various purposes such as inhibition of irradiation. As the filter dyes, there may be used dyes for further reducing photographic sensitivity, preferably ultraviolet absorbers having spectral absorption maxima in intrinsic sensitivity region of silver halide and dyes having substantial light absorption mainly in the region of 310–600 nm for increasing stability against safelight in handling the photosensitive materials as roomlight photosensitive materials. Depending on the purpose, these dyes are preferably added to emulsion layers or added together with a mordant to non-photosensitive hydrophilic colloid layers provided above the silver halide emulsion layer, namely, farther than the silver halide emulsion layer from the support and are fixed therein. These dyes are added in an amount of usually $10^{-3}$ to 1 g/m$^2$, preferably 10–500 mg/m$^2$ though it may vary depending on molar extinction coefficient of the dyes. The dyes can be added to coating solutions as solutions in suitable solvents such as water, alcohols such as methanol and ethanol, acetone, methyl cellosolve or mixtures thereof. These dyes may also be used in combination of two or more. Examples of these dyes are described in Japanese Patent Kokai No.63-64039. In addition, there may also be used ultraviolet absorbing dyes described in U.S. Pat. Nos. 3,314,794, 3,352,681, 3,499,762, 3,533,794, 3,700,455, 3,705,805, 3,707,375 and 4,045,229, Japanese Patent Kokai Nos. 46-2784 and 2-293839, and West German Patent Publication No. 1,547,863. Moreover, there may also be used pyrazolone oxonol dyes described in U.S. Pat. No. 2,274,782 and Japanese Patent Kokai Nos.62-185755 and 63-2045, diarylazo dyes described in U.S. Pat. No. 2,956,879, styryl dyes and butadienyl dyes described in U.S. Pat. Nos. 3,423,207 and 3,384,487, merocyanine dyes described in U.S. Pat. No. 2,527,583, merocyanine dyes and oxonol dyes described in U.S. Pat. No. 3,486,897, 3,652,284 and 3,718,472, enaminohemioxonol dyes described in U.S. Pat. No. 3,976,661, and dyes described in British Patent Nos. 584,609 and 1,177,429, Japanese Patent Kokai Nos. 48-85130, 49-99620, 49-114420 and 62-133453, and U.S. Pat. Nos. 2,533,472, 3,148,187, 3,177,078, 3,247,127, 3,540,887, 3,575,704 and 3,653,905.

In order to obtain photographic characteristics of super-high contrast using the silver halide photosensitive materials of the present invention, there is no need to use the conventional lith developers or high alkali developers having a pH close to 13 described in U.S. Pat. No. 2,419,975, and stable developers can be used. That is, for processing the silver halide photographic photosensitive materials of the present invention, developers containing sufficient sulfite ion (especially, 0.15 mol/l or more) as a preservative can be used and furthermore, negative images of sufficiently super-high contrast can be obtained with developers having a pH of 9.5 or higher, especially 10.0–11.0. Developing agents usable in the method of the present invention have no special limitation and examples thereof are dihydroxybenzenes such as hydroquinone, 3-pyrazolidones such as 1-phenyl-3-pyrazolidone and 4,4-dimethyl-1-phenyl-3-pyrazolidone, and aminophenols such as N-methyl-paminophenol. These may be used each alone or in combination of two or more. The silver halide photosensitive materials of the present invention are especially suitable to be processed with a developer containing dihydroxybenzenes as a main developing agent and 3-pyrazolidones or aminophenols as an auxiliary developing agent. Preferably, the developer contains 0.05–0.5 mol/l of dihydroxybenzenes and 0.06 mol/l or less of 3-pyrazolidones or aminophenols.

It is also possible to add amines to developers as described in U.S. Pat. No. 4,269,929 to increase developing rate to realize shortening of developing time. The developers can further contain pH buffers such as sulfites, carbonates, borates and phosphates of alkali metals, and development retarders and antifoggants such as bromides, iodides and organic antifoggants (especially preferably, nitroindazoles and benzotriazoles). Furthermore, the developers may contain water softeners, dissolving aids, color toning agents, development promotors, surface active agents (especially preferably the above-mentioned polyalkylene oxides), antifoamers, hardeners and silver sludge inhibitors for films (such as 2-mercaptobenzimidazolesulfonic acid). The processing temperature for the present invention is usually 18°–50° C. It is preferred to use an automatic processor for photographic processing and even when the total processing time from putting the photosensitive material into the automatic processor until it is discharged from the automatic processor is set at 90–120 seconds, photographic characteristics of sufficiently superhigh contrast negative tone can be obtained. The compounds described in Japanese Patent Kokai No. 56-24347 can be used in developers of the present invention as silver sludge inhibitors. As dissolving aids added to developers, there may be used the compounds described in Japanese Patent Kokai No. 61-267759. Moreover, as pH buffers used in developers, there may be used the compounds described in Japanese Patent Kokai No. 60-93433 or those described in Japanese Patent Kokai No. 62-186259.

The following nonlimiting examples will explain the present invention.

EXAMPLE 1

1) Preparation of coated samples:

An aqueous silver nitrate solution and an aqueous sodium chloride solution were simultaneously mixed with an aqueous gelatin solution kept at 40° C. in the presence of $(NH_4)_3RhCl_6$ in an amount of $5.0 \times 10^{-6}$ mol per 1 mol of silver. Then, the soluble salt was removed by a method well known in the art, followed by adding gelatin and 2-methyl-4-hydroxy-1,3,3a,7-tetrazaindene as a stabilizer without chemical ripening. The resulting emulsion was monodispersed emulsion having an average grain size of 0.2 μ and having a cubic crystal form. To this emulsion was added each of the hydrazine compounds of the formulas (I) and (II) shown in Tables 1 and 2 and the following comparative compounds (A), (B), (C) and (D) in an amount as shown in Tables 1 and 2. Then, to the emulsion were added 10 mg/m² of the following compound (X) as a nucleation promotor, 30% by weight (solid content based on gelatin) of polyethyl acrylate latex, and 1,3-divinylsulfonyl-2-propanol as a hardener. The emulsion was coated on a polyester film at a coating amount of 3.8 g/m² in terms of Ag. Coating amount of gelatin was 1.8 g/m². Thereon was coated a protective layer comprising 1.5 g/m² of gelatin and 0.3 g/m² of polymethyl methacrylate having a particle size of 2.5 μ.

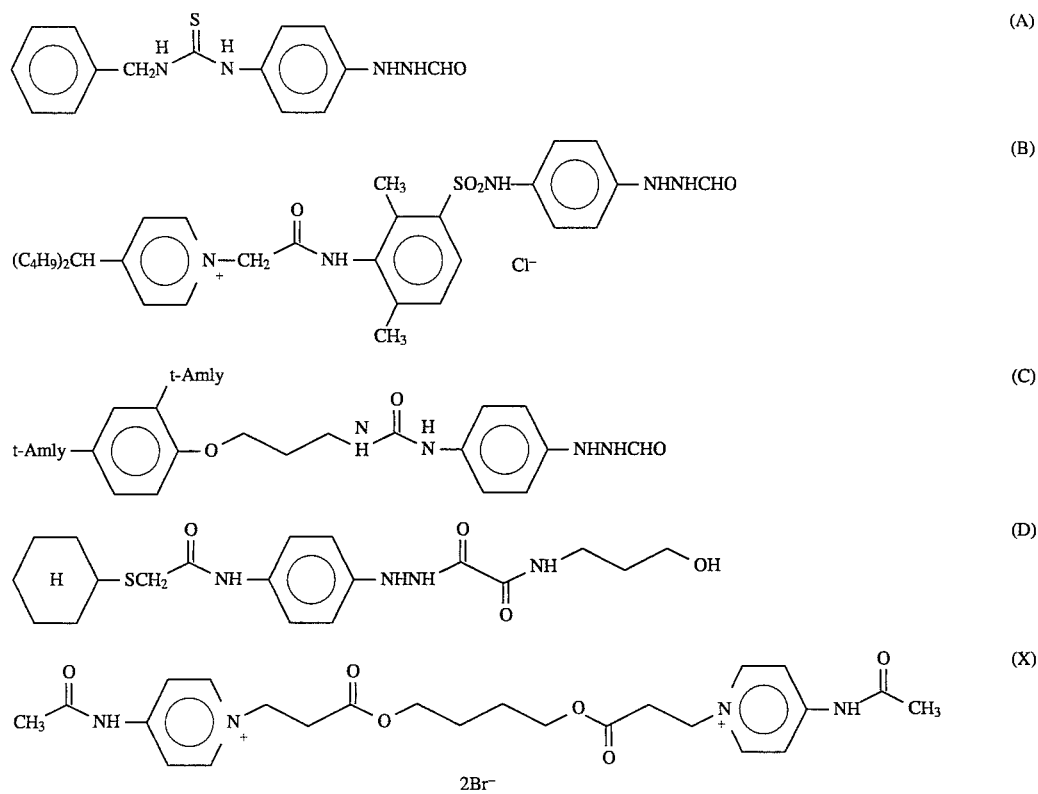

The resulting coated sample was imagewise exposed by a roomlight printer P-627GA manufactured by Dainippon Screen Mfg. Co., Ltd., developed with the following developer-1 at 35° C. for 30 seconds, fixed with a fixer PURCF901 manufactured by Mitsubishi Paper Mills Ltd., washed with water and dried. Dmax of each sample and results of evaluation of letter image quality are shown in Tables 1 and 2. The letter image quality 5 means that when the sample was subjected to a correct exposure using a dot original so that a dot area of 50% of the original occupies a dot area of 50% on a reversing photosensitive material, a letter of 30 μm in width can be reproduced, and this indicates very good quality. The letter image quality 1 means that when the sample is subjected to the same correct exposure as above, only a letter of more than 150 μm in width can be reproduced, and this indicates an inferior quality. Ranks of 4–2 are provided between 5 and 1 in accordance with organoleptic evaluation. The ranks 3 or more are practically acceptable levels. Dmax is a maximum density when exposure is similarly conducted so that a dot area of 50% of the original occupies a dot area of 50%. The samples of the present invention had a high Dmax and were excellent in letter image quality. Furthermore, the compounds of the present invention effectively acted with a smaller amount than the comparative compounds.

| [Developer-1] | |
|---|---|
| Hydroquinone | 30.0 g |
| 4-Hydroxymethyl-4-methyl-1-phenyl-3-pyrazolidone | 0.3 g |
| Sodium sulfite | 75.0 g |
| EDTA.2Na | 1.0 g |
| Tripotassium phosphate | 80.0 g |
| Potassium bromide | 2.0 g |
| Sodium hydroxide | 13.0 g |
| 5-Methylbenzotriazole | 0.3 g |
| 1-Diethylamino-2,3-dihydroxypropane | 17.0 g |
| Sodium p-toluenesulfonate | 7.0 g |
| Water was added to make up 1 liter in total. | |
| pH was adjusted to 11.0 with potassium hydroxide. | |

TABLE 1

| Sample No. | Compound | Amount (mol/Agmol) | Dmax | Letter image quality | Note |
|---|---|---|---|---|---|
| 1 | (A) | $0.35 \times 10^{-3}$ | 2.0 | 3 | Comparative sample |
| 2 | " | $0.7 \times 10^{-3}$ | 3.1 | 4 | Comparative sample |
| 3 | " | $1.4 \times 10^{-3}$ | 3.3 | 4 | Comparative sample |
| 4 | (B) | $0.35 \times 10^{-3}$ | 2.1 | 2 | Comparative sample |
| 5 | " | $0.7 \times 10^{-3}$ | 3.3 | 3 | Comparative sample |
| 6 | " | $1.4 \times 10^{-3}$ | 3.2 | 3 | Comparative sample |
| 7 | (C) | $0.35 \times 10^{-3}$ | 2.2 | 1 | Comparative sample |
| 8 | " | $0.7 \times 10^{-3}$ | 3.3 | 2 | Comparative sample |
| 9 | " | $1.4 \times 10^{-3}$ | 3.5 | 2 | Comparative sample |
| 10 | (D) | $0.35 \times 10^{-3}$ | 1.8 | 2 | Comparative sample |
| 11 | " | $0.7 \times 10^{-3}$ | 2.2 | 2 | Comparative sample |
| 12 | " | $1.4 \times 10^{-3}$ | 2.8 | 2 | Comparative sample |

TABLE 2

| Sample No. | Compound | Amount (mol/Agmol) | Dmax | Letter image quality | Note |
|---|---|---|---|---|---|
| 13 | (2) | $0.2 \times 10^{-3}$ | 3.3 | 3 | The present invention |
| 14 | " | $0.4 \times 10^{-3}$ | 3.9 | 4 | The present invention |
| 15 | " | $0.6 \times 10^{-3}$ | 4.8 | 5 | The present invention |
| 16 | (3) | $0.2 \times 10^{-3}$ | 3.2 | 3 | The present invention |
| 17 | " | $0.4 \times 10^{-3}$ | 3.7 | 4 | The present invention |
| 18 | " | $0.6 \times 10^{-3}$ | 4.4 | 4 | The present invention |
| 19 | (6) | $0.2 \times 10^{-3}$ | 4.3 | 4 | The present invention |
| 20 | " | $0.5 \times 10^{-3}$ | 5.0 | 5 | The present invention |
| 21 | (9) | $0.2 \times 10^{-3}$ | 4.0 | 4 | The present invention |
| 22 | " | $0.5 \times 10^{-3}$ | 5.1 | 5 | The present invention |
| 23 | (19) | $0.2 \times 10^{-3}$ | 4.3 | 4 | The present invention |
| 24 | " | $0.5 \times 10^{-3}$ | 5.0 | 5 | The present invention |

EXAMPLE 2

1) Preparation of coated samples

A silver iodobromide emulsion comprising cubic crystals of 0.25 μ in average grain size and containing 97 mol % of AgBr and 3 mol % of AgI was prepared by double jet method in the presence of $4 \times 10^{-7}$ mol of potassium hexachloroiridate (III) per 1 mol of silver and ammonia. The emulsion was subjected to desalting by flocculation method and thereto was added 40 g of inert gelatin per 1 mol of silver. To this emulsion kept at 50° C. was added 5,5'-dichloro-9-ethyl-3,3'-bis(4-sulfobutyl)oxacarbocyanine as a sensitizing dye and the emulsion was left to stand for 20 minutes and then cooled. To this emulsion was added each of the compounds of the present invention shown in Tables 3 and 4 and the comparative compounds (A), (B), (C) and (D) and furthermore, thereto were added 5-methylbenzothiazole and 2-methyl-4-hydroxy-1,3,3a,7-tetraazaindene. Moreover, to each of the samples were added 20 mg/m² of the compound (X) and 30 mg/m² of the following compound (Y) as high contrast promotor and was further added 1,3-divinylsulfonyl-2-propanol. The emulsion was coated on a polyethylene terephthalate film at a coating amount of 3.7 g/m² in terms of silver. Thereon was coated 1.5 g/m² of gelatin as a protective layer to obtain samples.

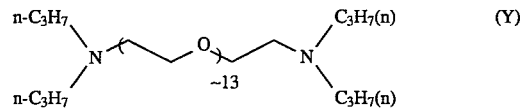

2) Evaluation of photographic properties

These samples were exposed through an optical wedge and a gray contact screen of 150 lines to tungsten light of 3200°K., developed with the following developer-2 at 35° C. for 30 seconds, fixed, washed with water and dried. Dot quality and Dmax of the resulting samples are shown in Tables 3 and 4. The dot quality was visually evaluated in five ranks. The rank 5 means the best quality and 1 means the worst quality. For making printing plates, the samples of ranks 5 and 4 are practically usable, those of rank 3 are inferior, but can barely be used, and those of ranks 2 and 1 are practically unusable. Dmax was obtained in the following manner. The samples were exposed through an optical wedge as above and developed. The Dmax is shown by the optical density of a point which is exposed with an exposure greater by 0.5 than an exposure (logE) which gives an optical density of 1.5, namely, an exposure of 0.5+logE. It can be seen that the compounds of the present invention can give good dot quality with maintaining a high Dmax with a smaller amount than the comparative compounds.

| [Developer-2] | |
|---|---|
| Hydroquinone | 30.0 g |
| 4-Hydroxymethyl-4-methyl-1-phenyl-3-pyrazolidone | 0.3 g |
| Potassium hydroxide | 20.0 g |
| Sodium hydroxide | 18.0 g |
| Sodium sulfite | 30.0 g |
| EDTA.2Na | 1.0 g |
| Potassium bromide | 10.0 g |
| 5-Methylbenzotriazole | 0.4 g |
| 5-Benzenesulfonamide-2-mercaptobenzimidazole | 0.5 g |
| Water was added to make up 1 liter in total. | |
| pH was adjusted to 10.5. | |

TABLE 3

| Sample No. | Compound | Amount (mol/Agmol) | Dmax | Letter image quality | Note |
|---|---|---|---|---|---|
| 25 | (A) | $0.35 \times 10^{-3}$ | 3.6 | 2 | Comparative sample |
| 26 | " | $0.7 \times 10^{-3}$ | 4.0 | 2 | Comparative sample |
| 27 | " | $1.4 \times 10^{-3}$ | 4.5 | 3 | Comparative sample |
| 28 | (B) | $0.35 \times 10^{-3}$ | 3.5 | 2 | Comparative sample |
| 29 | " | $0.7 \times 10^{-3}$ | 4.9 | 3 | Comparative sample |
| 30 | " | $1.4 \times 10^{-3}$ | 5.1 | 3 | Comparative sample |
| 31 | (C) | $0.35 \times 10^{-3}$ | 3.2 | 1 | Comparative sample |
| 32 | " | $0.7 \times 10^{-3}$ | 3.7 | 2 | Comparative sample |
| 33 | " | $1.4 \times 10^{-3}$ | 4.0 | 2 | Comparative sample |
| 34 | (D) | $0.35 \times 10^{-3}$ | 2.8 | 1 | Comparative sample |
| 35 | " | $0.7 \times 10^{-3}$ | 4.2 | 2 | Comparative sample |
| 36 | " | $1.4 \times 10^{-3}$ | 4.7 | 2 | Comparative sample |

TABLE 4

| Sample No. | Compound | Amount (mol/Agmol) | Dmax | Letter image quality | Note |
|---|---|---|---|---|---|
| 37 | (2) | $0.2 \times 10^{-3}$ | 3.7 | 3 | The present invention |
| 38 | " | $0.4 \times 10^{-3}$ | 4.4 | 4 | The present invention |
| 39 | " | $0.6 \times 10^{-3}$ | 5.7 | 5 | The present invention |
| 40 | (3) | $0.2 \times 10^{-3}$ | 3.4 | 3 | The present invention |
| 41 | " | $0.4 \times 10^{-3}$ | 4.4 | 4 | The present invention |
| 42 | " | $0.6 \times 10^{-3}$ | 5.2 | 5 | The present invention |
| 43 | (6) | $0.2 \times 10^{-3}$ | 4.5 | 4 | The present invention |
| 44 | " | $0.5 \times 10^{-3}$ | 5.3 | 5 | The present invention |
| 45 | (9) | $0.2 \times 10^{-3}$ | 4.3 | 4 | The present invention |
| 46 | " | $0.5 \times 10^{-3}$ | 5.5 | 5 | The present invention |
| 47 | (19) | $0.2 \times 10^{-3}$ | 4.8 | 4 | The present invention |
| 48 | " | $0.5 \times 10^{-3}$ | 5.3 | 5 | The present invention |

What is claim is:

1. A silver halide photographic photosensitive material which comprises a support and, provided thereon, at least one hydrophilic colloid layer including a silver halide emulsion layer, said photosensitive material containing at least one compound represented by the following formula (I) and (II):

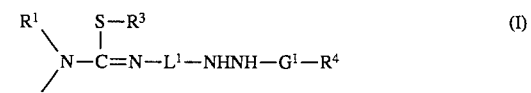

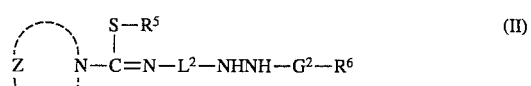

wherein $L^1$ and $L^2$ each represent a divalent linkage group, $G^1$ and $G^2$ each represent a carbonyl group, a sulfonyl group, a sulfinyl group, an oxalyl group or a phosphoryl group, $R^1$ and $R^2$ each represent a hydrogen atom, an alkyl group, an aralkyl group, an alkenyl group or an aryl group, $R^3$ and $R^5$ each represent an alkyl group, an aralkyl group or an alkenyl group, $R^4$ and $R^6$ each represent a hydrogen atom, an alkyl group, an alkoxy group, an aryloxy group, an aryl group or an amino group, Z represents a group of atoms necessary to form a nitrogen-containing 5- to 18-membered ring, X represents a counter ion, and m and n each represent 0 or 1, and the isothioureido group may be a salt of a protonic acid.

2. A silver halide photographic photosensitive material according to claim 1, wherein the silver halide emulsion layer or other hydrophilic colloid layer contains the compound represented by the formula (I) and (II).

3. A silver halide photographic photosensitive material according to claim 1, wherein the content of the compound represented by the formula (I) and (II) is $1 \times 10^{-6}$ to $1 \times 10^{-2}$ mol per 1 mol of silver in the silver halide emulsion layer.

4. A silver halide photographic photosensitive material according to claim 1, wherein the silver halide emulsion layer is a surface latent image type silver halide emulsion layer.

5. A method of developing the silver halide photographic photosensitive material of claim 1 with a developer having a pH of 10.0–11.0.

* * * * *